United States Patent [19]
Bombardelli et al.

[11] Patent Number: 5,648,377
[45] Date of Patent: Jul. 15, 1997

[54] FORMULATIONS CONTAINING CAROTENOIDS AN PROCAROTENOIDS COMBINED WITH POLYPHENOLS IN THE PREVENTION OF THE DAMAGES DUE TO AN ABNORMAL PRODUCTION OF FREE RADICALS

[75] Inventors: Ezio Bombardelli; Paolo Morazzoni, both of Milan, Italy

[73] Assignee: Indena S.p.A., Milan, Italy

[21] Appl. No.: 463,129

[22] Filed: Jun. 5, 1995

Related U.S. Application Data

[63] Continuation-in-part of Ser. No. 243,855, May 17, 1994, abandoned.

[30] Foreign Application Priority Data

Dec. 21, 1993 [IT] Italy .................. MI93A2688

[51] Int. Cl.$^6$ .................. A61K 31/35; A61K 31/355
[52] U.S. Cl. .................. 514/456; 514/458; 514/725; 514/764; 514/886; 424/430; 424/436; 424/449; 424/451; 424/456; 424/464; 424/DIG. 15
[58] Field of Search .................. 424/195.1, 451, 424/456, 464, 430–436, 449, DIG. 15; 514/458, 725, 764, 456, 886

[56] References Cited

U.S. PATENT DOCUMENTS

| | | | |
|---|---|---|---|
| 4,362,494 | 12/1982 | Zysman et al. | 424/401 |
| 4,749,573 | 6/1988 | Bonne et al. | 424/195.1 |
| 4,801,960 | 1/1989 | Goetz et al. | 424/465 |
| 4,997,649 | 3/1991 | Papaconstantin et al. | 424/195.1 |
| 5,001,115 | 3/1991 | Sloan | 514/34 |
| 5,073,379 | 12/1991 | Klimesch et al. | 424/467 |

*Primary Examiner*—John W. Rollins
*Attorney, Agent, or Firm*—Bucknam and Archer

[57] ABSTRACT

The present invention relates to novel formulations and combinations of lipophilic and hydrophilic antioxidants and the use thereof in the therapeutic, foodstuff, dietetic, and cosmetic fields. These formulations are based on the use of carotenoids, procarotenoids and derivatives thereof with polyphenols of catechic structures. Said formulations, containing a lipophilic antioxidant and an hydrophilic one, can be used in the prevention of physiopatological conditions related at least partially to an over-production of free radicals, particularly aging, atherosclerosis and cancer.

9 Claims, 1 Drawing Sheet

Figure 1 - Inhibition of LDL oxidation by 90% Procyanidolic oligomers from Vitis vinifera and Lycopene
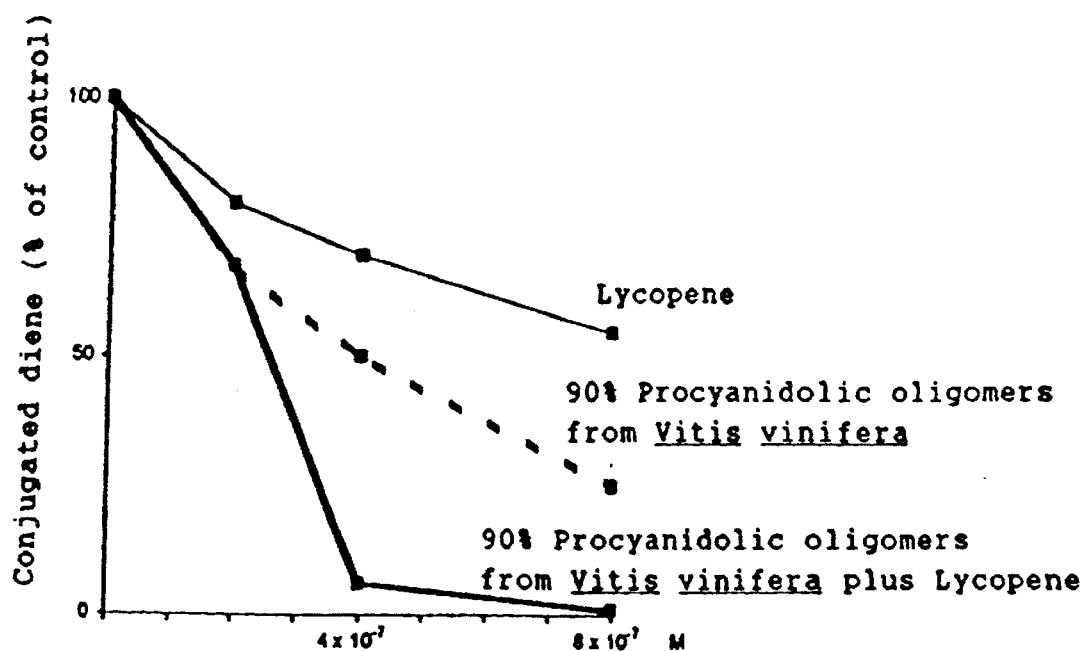

FORMULATIONS CONTAINING CAROTENOIDS AN PROCAROTENOIDS COMBINED WITH POLYPHENOLS IN THE PREVENTION OF THE DAMAGES DUE TO AN ABNORMAL PRODUCTION OF FREE RADICALS

This application is a continuation-in-part of U.S. Ser. No. 08/243,855, filed May 17, 1994 now abandoned.

FIELD OF THE INVENTION

The present invention relates to novel formulations and combinations of lipophilic and hydrophilic antioxidants and the use thereof in the therapeutic, foodstuff and cosmetic fields. These formulations are based on the use of carotenoids, procarotenoids (and derivatives thereof) with polyphenols of catechin structures, both pure and contained in extracts.

DESCRIPTION OF THE PRIOR ART

It is well established in literature that the administration of vitamin E, β-carotene, lycopene and ubidecarenone (Coenzyme Q 10) through the diet or in pharmaceutical and nutritional formulations significantly decreases the incidence of cardiovascular diseases, and also it seems to play an important role in the prevention of some tumors. As far as the anti-aterosclerotic activity of carotenoids is concerned, according to recent studies, the capability of carotenoids to prevent lipoproteins oxidation (therefore interfering with the vasal uptake thereof) appears to be one of the most important mechanisms. In fact, carotenoids are incorporated physiologically in low density lipoproteins (LDL) and, preventing the oxidation thereof, they effectively counteract the primum movens of the aterosclerotic damage, which occurs mainly to the detriment of endothelial tissue (Ziegler R. G., A review of epidemiologic evidence that carotenoids reduce the risk of cancer, J. Nutr. 119, 116–122, 1989; Block G., Patterson B., Subar A., Fruits, vegetables and cancer prevention: a review of the epidemiological evidence, Nutr. Cancer. 18, 1–29, 1992; Frankel E. N., Kanner J., German J. B., Parks E., Kinsella J. E., Inhibition of oxidation of human low-density lipoprotein by phenolic substances in red wine, The Lancet 341, 454–457, 1993; Esterbauer H., Dieber-Rotheneder M., Waeg G., Striegl G., Jurgens G., Biochemical, structural and functional properties of oxidized low-density lipoproteins, Chem. Rex. Toxicol. 3, 77–92, 1990).

Carotenoids are effective antioxidants at the cell level, their function taking place particularly on the cell in active proliferation, in which the frequency of genic error is higher. In support of carotenoids bioavailability, the preventive action thereof, after oral administration, against skin damage due to ultra-violet radiation, which are known to give rise to oxygen radicals, as well as the role thereof at the peripheral level on the eye functions, are well known.

Polyphenol substances having a catechin structure of the dimeric and oligomeric types are widely used in cardiovascular therapy and in ophthalmology due to their action on large and small calibre vessels. These natural polyphenols exert in fact a beneficial modulating action on capillary fragility and permeability, as well as on the protection of endotheliums. Recent literature agrees in considering the antioxidant activity an important mechanism at the base of the biological effect of said compounds.

As recently proved by the Applicant for the procyanidole oligomers extracted from Vitis Vinifera (Liviero L., Puglisi P. P., Bombardelli E., Morazzoni P., Aldini G.C., Carini M., Maffei-Facino R., Antimutagenic activity of antioxidant procyanidins from Vitis vinifera, In: International Symposium of the Phytochemical Society of Europe—Phytochemistry of Plants used in Traditional Medicine, University of Lausanne, 29 Sep.–1 Oct. 1993. In press on Mutation Research) and by other authors for a number of polyphenolic substances extracted from different vegetable sources (Hayatsu H., Arimoto S., Negishi T., Dietary inhibitors of mutagenesis and carcinogenesis., Mutation Res. 202, 429, 1988; Cassady J. M., Natural products as a source of potential cancer chemotherapeutic and chemopreventive agents., J. Nat. Prod. 53, 23, 1990), another interesting biological property of this series of compounds is that they have a remarkable antimutagenic action. Such a characteristic, which is partly connected with the antioxidant effect, takes place both on spontaneous mutagenesis and on the one induced either by ultraviolet radiation or by mutagenic products such as medicaments or atmospheric pollutants.

The action sites of the polyphenolic substances are very different from those of carotenoids and analogues thereof, therefore the concomitant administration of lipophilic and hydrophilic compounds gives rise to an unexpected, surprising advantage from the biological point of view.

Carotenoids such as vitamin E, β-carotene, lycopene, coenzyme Q10 and isomers thereof proved to be very effective antiradical compounds against the activated forms of oxygen, both in the conventional tests of lipid peroxidation, such as the xanthine—xanthine oxidase system, and in a very selective model, which involves lipid peroxidation of an unsaturated phospholipid in an aqueous medium by means of ultrasound (Maffei-Facino R., Carini M., Aldini G., Bombardelli E., Morazzoni P., Morelli R., Free radicals scavenging action and anti-enzyme activities of procyanidines from Vitis vinifera: a mechanism for their capillary protective action, Arzneim. Forsch./Drug. Res., in press.). In the same tests, the polyphenols of the invention turned out to have the same or a higher activity than the prior art compounds.

The results obtained from these tests, using some polyphenolic substances and the lipophilic antioxidants Vitamin E and lycopene, are summarized in Tables 1 and 2.

TABLE 1

| Scavenger activity against the OH° Hydroxy radical - Inductive phase. | |
|---|---|
| Substances | CI$_{50}$ |
| Proanthocyanidin A2 | $1.7 \times 10^{-7}$ |
| 90% Procyanidole oligomers from Vitis vinifera | $1.1 \times 10^{-7}$ |
| Vitamin E | $1.5 \times 10^{-6}$ |
| Lycopene | $2.1 \times 10^{-6}$ |

TABLE 2

| Scavenger activity against R°, ROO° lipid radicals. Propagation phase. | |
|---|---|
| Substances | CI$_{50}$ |
| Proanthocyanidin A2 | $4.0 \times 10^{-7}$ |
| 90% Procyanidole oligomers from Vitis vinifera | $5.1 \times 10^{-7}$ |
| Vitamin E | $1.0 \times 10^{-7}$ |

TABLE 2-continued

Scavenger activity against R°, ROO° lipid radicals. Propagation phase.

| Substances | $CI_{50}$ |
|---|---|
| Lycopene | $1.8 \times 10^{-7}$ |
| Lycopene + Proc. olig. from Vitis vinifera 1:4 | $1.2 \times 10^{-9}$ |

SUMMARY OF THE INVENTION

It has surprisingly been found, and it is one object of the present invention, that the combination of a hydrophilic antioxidant with a lipophilic one exerts an antioxidant action far greater than that of the sum of the single compounds tested at equal concentrations (Table 2).

This finding was confirmed in another in vitro model which uses human fibroblasts stimulated with zymosan and evaluation of the peroxidative process by chemoluminescence. The results were obtained using a combination of lipophilic antioxidants (ubidecarenone, vitamin E) and hydrophilic antioxidants (oligomers extracted from Vitis vinifera).

Another significant test is the inhibition of oxidation of human LDL (Low Density Lipoprotein) by procyanidolic oligomers and lycopene. In the present test the capability of procyanidolic oligomers plus lycopene to inhibit LDL oxidation has been tested on human LDL oxidized by copper sulfate in comparison with separated procyanidolic oligomers and lycopene.

Blood was collected on EDTA from healthy volunteers and centrifuged at 1.500 g at 4° C. Plasma LDL were then prepared by sequential density ultracentrifugation in the presence of 0.01% EDTA and it was dialyzed with deoxygenated phosphate-buffered saline for 24 hours. The final concentration of LDL was diluted with phosphate-buffered (10 mmol/l) to a standard LDL protein concentration of 1 mg/ml.

The effects of increasing amounts of procyanidolic oligomers plus lycopene (and of the two compounds separated) on the oxidative susceptibility of LDL were investigated by measuring conjugated dienes formation (after ten minutes incubation with the polyphenols) by copper sulfate-catalysed oxidation of freshly prepared human LDL. For the conjugated dienes determination, we measured the absorption at 254 nm of dilute preparations of LDL containing 0.25 mg LDL protein/ml after oxidation for 1 h with 8 umol/l copper sulfate at room temperature (Esterbauer H., Striegl G., Puhl H., Rothneder M., Continue monitoring of in vitro oxidation of human low density lipoproteins. Free Rad. Res. Comm. 6, 67, 1989).

BRIEF DESCRIPTION OF DRAWINGS

FIG. 1 Inhibition of LDL oxidation by 90% Procyanidolic oligomers from Vitis vinifera and Lycopene.

As reported in FIG. 1, the generation of conjugated dienes by oxidation of LDL has been inhibited by ten minutes preincubation with the mixture procyanidolic oligomers plus lycopene. The mixture resulted to be more effective than the separated compounds.

The results obtained in the in vitro models using pure lycopene were subsequently confirmed by in vivo models in which the use of combinations of lipophilic antioxidants and hydrophilic antioxidants gave an effective, unpredictable improvement on the experimental damages in which free radicals play an important role.

As a control, we selected in fact an inflammatory process model in which an irritating agent phorbol ester is used, which triggers off lipid peroxidation at the level of biological membranes and subsequently propagates through a radical chain reaction.

Table 3 shows the data of the antioedemigenic activity in the mouse, obtained with procyanidolic oligomers from Vitis Vinifera combined with a lipophilic fraction having a high lycopene content (5%), the fraction being prepared by hexane extraction of dried skins of Licopersicum aesculentum and the fraction with lycopene. Data are expressed as percent decrease of the oedema measured at the 6th hour after the induction.

TABLE 3

Anti-oedemigenic activity of 90% Procyanidolic oligomers from Vitis Vinifera, Lycopene and combinations thereof on the phorbol ester oedema in the mouse.

| Substances | Dose μg/mouse | Oedema | % decrease |
|---|---|---|---|
| Controls | — | 7.9 ± 0.2 | — |
| 90% Procyanidolic oligomers from Vitis vinifera | 300 | 6.5 ± 0.2 | −17.7 NS |
|  | 150 | 7.5 ± 0.3 | −5.1 NS |
| 5% Lycopene | 200 | 6.9 ± 0.2 | −12.7 NS |
|  | 100 | 7.0 ± 0.3 | −11.4 NS |
| 5% Lycopene + 90% Procyanidolic oligomers from Vitis vinifera | 200 +100 | 1.1 ± 0.3* | −86.1 |
| 5% Lycopene + 90% Procyanidolic oligomers from Vitis vinifera | 100 +50 | 4.8 ± 0.1* | −39.2 | average ± SD
*p < 0.01

All the above reported data show that the combination of the two antioxidants of different polarity increases by far the effectiveness of the single compounds. Most likely, such synergism is due to the concomitant action on more radical species which gives rise to a nearly complete blockage of the peroxidative process.

The same phenomenon takes place when the antimutagenic effect of these combinations is checked, by which effect the antioxidant component plays a paramount role and which is of paramount importance due to the implications in the prevention of cancer and cardiovascular pathologies.

By way of example, in Table 4 the effect of polyphenols extracted from green tea, of lycopene and of a combination thereof is reported.

TABLE 4

Anti-mutagenic activity of procyanidol oligomers extracted from green tea, lycopene and a combination thereof on the frequency of spontaneous mutation in Salmonella typhimurium.

| Substance | TA98 | | TA100 | |
|---|---|---|---|---|
| mg/plate | −S9 | +S9 | −S9 | +S9 |
| 0 Proc. olig. | 1.0 (41) | 1.0 (48) | 1.0 (163) | 1.0 (133) |
| 1.0 | 1.0 | 0.8 | 0.9 | 1.0 |

TABLE 4-continued

Anti-mutagenic activity of procyanidol oligomers extracted from green tea, lycopene and a combination thereof on the frequency of spontaneous mutation in *Salmonella typhimurium*.

| Substance | TA98 | | TA100 | |
|---|---|---|---|---|
| mg/plate | −S9 | +S9 | −S9 | +S9 |
| 2.5 | 1.0 | 0.7 | 1.1 | 1.0 |
| 5.0 | 0.5 | 0.5 | 0.7 | 0.9 |
| Lycopene | | | | |
| 0.2 | 1.0 | 0.9 | 0.9 | 0.8 |
| 0.4 | 0.8 | 0.8 | 1.0 | 0.9 |
| 0.5 | 0.7 | 0.7 | 0.9 | 0.8 |
| Proc. olig. + Lycopene | | | | |
| 0.50 + 0.10 | 0.6 | 0.5 | 0.7 | 0.7 |
| 1.25 + 0.20 | 0.5 | 0.5 | 0.7 | 0.8 |
| 2.50 + 0.25 | 0.4 | 0.3 | 0.7 | 0.7 |

As the polyphenolic fraction from green tea, a product is used having an 85% polyphenol titre, expressed as epigallocatechin gallate, and a low caffeine content (<0.3%). Using mixtures of the lycopene fraction with tea polyphenols, inhibition of about 50% of spontaneous mutation was obtained in the Ames test (*Salmonella typhimurium* TA-100 and TA-98).

Such an effect turned out to be independent of the metabolic activation (−S9 or +S9). Analogous effects are obtained on *Saccharomyces cerevisiae* strains, where the effect on spontaneous mutation was controlled at the nuclear level and, even more important, at the level of mitochondrial information.

The ratios of the two fractions can vary from 1:1 to 1:10 part of lipophilic antioxidant with respect to polyphenol depending on the field of application of the different formulations.

As excipients for use in these formulations, particularly important are phospholipids, both the natural and the synthetic ones, and the raw lecithins having different phospholipid contents. Phospholipids are a particularly suitable carrier to promote adsorption of polyphenolic substances both of catechic and flavanolignan nature. The preferred administration forms of these combinations are soft gelatin capsules, but hard gelatin capsules, cellulose or other matrixes as well as suppositories and transdermal forms, can also be envisaged. The following examples further illustrate the invention.

Example I

Formulation Containing Procyanidol Oligomers and Lycopene in Peanut Oil 200 mg of lipophilic extract of *Licopersicum aesculentum* containing 5% of lycopene are mixed with 80 mg of procyanidol oligomers from *Vitis vinifera*, 50 mg of natural soy phosphatidylcholine and 50 mg of peanut oil; the products are encapsulated in soft gelatin capsules. The dose can vary from 1 to 5 capsules daily.

Example II

Formulation Containing Ubidecarenone and Procyanidol Oligomers 20 mg of ubidecarenone are mixed with 20 mg of vitamin E and 80 mg of procyanidol oligomers from green tea; this mixture is dispersed in 100 mg of peanut oil containing 50 mg of purified soy phospholipids. The suspension can be encapsulated in soft gelatin capsules or adsorbed on suitable excipients for the preparation of tablets. The dose can vary from 1 to 3 capsules daily.

Example III

Formulation Containing Ubiquinol (reduced Ubidecarenone), Unsaturated Phospholipids and Proanthocyanidin A2

20 mg of Ubiquinol are mixed with 100 mg of soy phosphatidylcholine and dissolved in 100 mg of peanut oil. This solution is added with 80 mg of Proanthocyanidin A2. The suspension can be incapsulated in soft gelatin capsules. The dose can vary from 1 to 3 capsules daily.

In another aspect, the present invention provides a method of treating a subject suffering from a disease, which is caused by an overproduction of free radicals, comprising the administration of a therapeutically effective amount of a composition according to the present invention.

In a further aspect, the present invention provides a method of treating a subject suffering from an inflammation.

In another aspect, the method according to the present invention is applicable to the treatment of a subject suffering from atheroschlerosis.

In yet another aspect, according to the invention there is provided a method for preventing the mutagenic activity induced by free radicals in a subject.

In still another aspect, the method of the present invention is useful for treating a subject suffering from a tumor.

We claim:

1. A composition comprising a lipophilic antioxidant in combination with a hydrophilic antioxidant, said lipophilic antioxidant being lycopene, said hydrophilic antioxidant being a procyanidol oligomer extracted from *Vitis vinifera*, said lycopene and said procyanidol oligomer extracted from *Vitis vinifera*, said lycopene and said procyanidol oligomer extracted from *Vitis vinifera* being in a ratio ranging from 1:1 to 1:10, said composition comprising at least one excipient, said composition exerting an antioxidant action greater than the sum of the antioxidant action of said lipophilic antioxidant and said hydrophilic antioxidant.

2. The composition according to claim 1 wherein said at least one excipient is a natural or a synthetic phospholipid or peanut oil.

3. The composition according to claim 2 wherein said phospholipid is a raw lecithin.

4. The composition according to claim 2 in the form of soft or hard gelatin capsule, tablet, suppository or in the transdermal form.

5. The composition according to claim 1 in the form of soft or hard gelatin capsule, tablet, suppository or in the transdermal form.

6. A method of treating a subject suffering from a disease, said disease being caused by an overproduction of free radicals, said method comprising the administration of a therapeutically effective amount of a composition comprising a lipophilic antioxidant in combination with a hydrophilic antioxidant, said lipophilic antioxidant being lycopene, said hydrophilic antioxidant being a procyanidol oligomer extracted from *Vitis vinifera*, said lycopene and said procyanidol oligomer extracted from *Vitis vinifera* being in a ratio ranging from 1:1 to 1:10, said composition comprising at least one excipient, said composition exerting an antioxidant action greater than the sum of the antioxidant action greater than the sum of the antioxidant action of said lipophilic antioxidant and said hydrophilic antioxidant.

7. The method according to claim 6 wherein said composition is in the form of capsules and each capsule contains 10 mgs of lycopene and 80 mgs of procyanidol oligomers from *Vitis vinifera*.

8. The method according to claim 6 wherein said composition is in the form of capsules and wherein each capsule further contains 20 mgs of ubidecarenone, 20 mgs of Vitamin E and 80 mgs of procyanidol oligomers from green tea.

9. The method according to claim 6 wherein said subject suffer from inflamation, atherosclerosis or a tumor.

* * * * *

UNITED STATES PATENT AND TRADEMARK OFFICE
CERTIFICATE OF CORRECTION

PATENT NO. : 5,648,377
DATED : July 15, 1997
INVENTOR(S) : Ezio Bombardelli, Paolo Morazzoni It is certified that error appears in the above-identified patent and that said Letters Patent is hereby corrected as shown below:

CLAIM 1, column 6, lines 38-39, delete "said lycopene and said procyanidol oligomer extracted from Vitis vinifera"

CLAIM 6, column 7, line 1, delete "greater than the sum of the antioxidant action"

Signed and Sealed this

Sixteenth Day of June, 1998

Attest:

BRUCE LEHMAN

Attesting Officer

Commissioner of Patents and Trademarks